United States Patent
Rietzel et al.

(10) Patent No.: US 8,657,743 B2
(45) Date of Patent: Feb. 25, 2014

(54) METHODS AND SYSTEMS FOR POSITION-ENABLED CONTROL OF A MEDICAL SYSTEM

(75) Inventors: Eike Rietzel, Darmstadt (DE); Andres Sommer, Langensendelbach (DE)

(73) Assignee: Seimens Aktiengesellschaft, München (DE)

( * ) Notice: Subject to any disclaimer, the term of this patent is extended or adjusted under 35 U.S.C. 154(b) by 835 days.

(21) Appl. No.: 12/201,700

(22) Filed: Aug. 29, 2008

(65) Prior Publication Data

US 2009/0069640 A1    Mar. 12, 2009

(30) Foreign Application Priority Data

Sep. 6, 2007   (DE) .......................... 10 2007 042 337

(51) Int. Cl.
*A61B 5/00*    (2006.01)
*A61B 6/00*    (2006.01)
*A61B 6/10*    (2006.01)
*G06F 19/00*   (2011.01)
*H04B 1/20*    (2006.01)

(52) U.S. Cl.
CPC ... *A61B 6/00* (2013.01); *A61B 6/10* (2013.01); *A61B 6/4411* (2013.01); *A61B 6/581* (2013.01); *G06F 19/3418* (2013.01); *H04B 1/202* (2013.01)
USPC ............. 600/301; 600/407; 378/65; 378/116; 340/539.12; 340/539.13; 340/5.2; 340/8.1; 340/12.22

(58) Field of Classification Search
USPC ............. 340/870.01–870.02, 870.07, 870.16, 340/870.18, 870.25–870.28, 500, 524, 529, 340/531, 532, 539.12–539.32, 540, 286.01, 340/286.07, 999, 3.54; 600/300–301, 1–8; 378/145–161, 210, 193–203; 709/223–226
See application file for complete search history.

(56) References Cited

U.S. PATENT DOCUMENTS

| | | | | |
|---|---|---|---|---|
| 5,206,894 | A | * | 4/1993 | Makrinos et al. ................ 378/93 |
| 5,555,120 | A | * | 9/1996 | Telymonde et al. .......... 398/111 |
| 6,219,403 | B1 | * | 4/2001 | Nishihara ........................ 378/65 |

(Continued)

FOREIGN PATENT DOCUMENTS

| | | |
|---|---|---|
| DE | 101 16 870 A1 | 10/2001 |
| DE | 10 2004 027 159 A1 | 1/2005 |

(Continued)

OTHER PUBLICATIONS

European Patent Office Action dated Jan. 12, 2009 with English translation.

(Continued)

*Primary Examiner* — Bill Thomson
*Assistant Examiner* — Marie Archer
(74) *Attorney, Agent, or Firm* — Lempia Summerfield Katz LLC

(57) ABSTRACT

A control device for a medical system is provided. The medical system may be a medical diagnosis and/or medical therapy system. The medical system may include a control unit operable to be used to carry out control processes that control the medical system, and a mobile handheld control unit operable to control at least one controllable element of the medical system by a user. The control device may be configured so that one or more control processes may only be carried out by the control unit when the mobile handheld control unit is located at a predefined location.

14 Claims, 2 Drawing Sheets

(56) References Cited

U.S. PATENT DOCUMENTS

| | | |
|---|---|---|
| 6,689,091 B2 * | 2/2004 | Bui et al. .................... 604/67 |
| 6,768,425 B2 * | 7/2004 | Flaherty et al. .......... 340/870.07 |
| 6,961,604 B1 * | 11/2005 | Vahasalo et al. ............. 600/410 |
| 7,227,493 B2 * | 6/2007 | Oswald et al. ................. 342/70 |
| 7,502,444 B2 * | 3/2009 | Marar .......................... 378/98 |
| 7,835,498 B2 * | 11/2010 | Bonfiglio et al. ............ 378/115 |
| 2002/0087048 A1 | 7/2002 | Brock et al. |
| 2002/0131553 A1 * | 9/2002 | Tsuchino ...................... 378/118 |
| 2002/0164997 A1 * | 11/2002 | Parry ........................... 455/456 |
| 2005/0004630 A1 * | 1/2005 | Kagermeier et al. ........... 607/60 |
| 2005/0065417 A1 | 3/2005 | Ali et al. |
| 2005/0251228 A1 * | 11/2005 | Hamel ............................ 607/60 |
| 2007/0114471 A1 * | 5/2007 | Birgy et al. ................ 250/505.1 |

FOREIGN PATENT DOCUMENTS

| | | |
|---|---|---|
| DE | 103 36 731 A1 | 3/2005 |
| DE | 10 2004 048067 A1 | 4/2006 |
| DE | 10 2005 021 604 A1 | 11/2006 |
| DE | 10 2005 033 957 A1 | 2/2007 |
| WO | WO 2005/018242 A2 | 2/2005 |
| WO | WO 2005110208 A1 * | 11/2005 |
| WO | WO 2007/009881 A2 | 1/2007 |

OTHER PUBLICATIONS

German Office Action dated Jun. 19, 2008 with English translation.

* cited by examiner

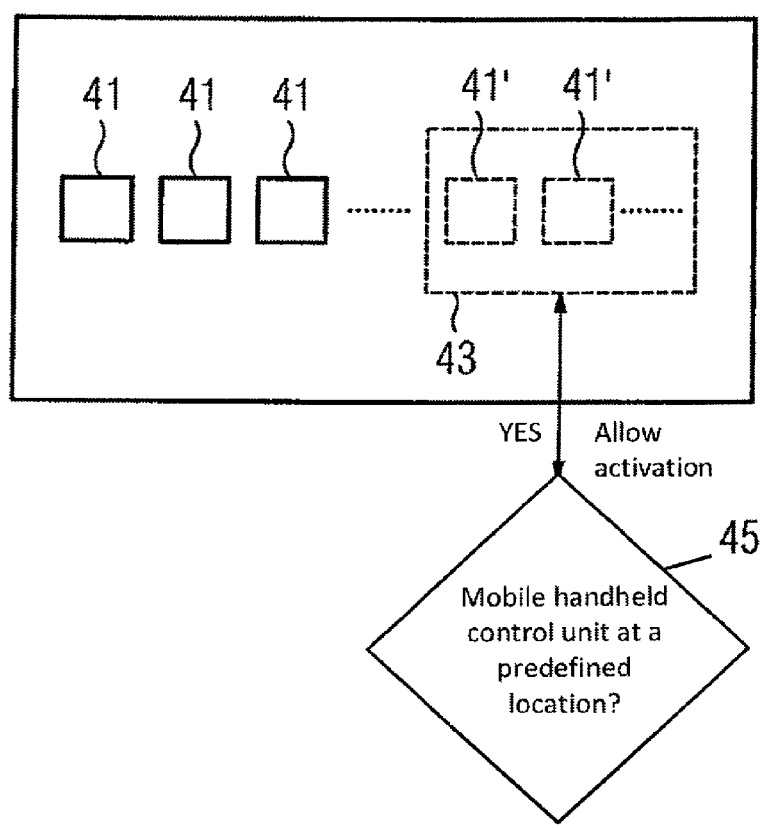

METHODS AND SYSTEMS FOR POSITION-ENABLED CONTROL OF A MEDICAL SYSTEM

This application claims the benefit of DE 10 2007 042 337.5, filed Sep. 6, 2007, which is hereby incorporated by reference.

BACKGROUND

The present embodiments relate to control of a medical diagnosis and/or therapy system.

The description which follows uses the example of particle therapy and is based on a particle therapy system but can be applied without further ado to other medical diagnosis and/or therapy systems.

Particle therapy may be used to treat tissue, such as tumorous diseases. Radiation methods, which are used in particle therapy, may be used in non-therapeutic areas, such as research work in the context of particle therapy, which is carried out on non-living phantoms or bodies or material irradiation. Charged particles are accelerated to high energies, formed into a particle beam, and guided to one or more radiation rooms by a high-energy beam transportation system. The object to be irradiated is irradiated with the particle beam in one of these radiation rooms.

In a particle therapy system, different components execute different acts that are coordinated precisely with one another. The various components are controlled by a control device, which ensures correct interaction of the individual components and correct functioning of the particle therapy system.

A set of the control process of a particle therapy system may be carried out by a user with the aid of a mobile handheld control unit. Such a handheld control unit may be deployed when a user is in a treatment room of a particle therapy system, for example, to prepare a patient for a subsequent radiation session. A user may, for example, use the handheld control unit to operate the patient positioning device on which the patient is located or to set settings of the particle therapy system using the handheld control unit. Using the mobile handheld control unit, the user can carry out control operations from different locations, for example, in direct proximity to the patient, without having to keep going to a permanently installed controller.

SUMMARY AND DESCRIPTION

The present embodiments may obviate one or more of the problems or drawbacks inherent in the related art. For example, in one embodiment, a control device may control a medical diagnosis and/or therapy system. The control device allows safe operation of the medical diagnosis and/or therapy system when using a mobile handheld control unit. In another example, a medical diagnosis and/or therapy system includes a control device. In yet another example, a method is provided for controlling a medical diagnosis and/or therapy system, which allows safe control of the medical diagnosis and/or therapy system even when using a mobile handheld control unit.

In one embodiment, a control device for a medical diagnosis and/or therapy system is provided. The control device includes a control unit and a mobile handheld control unit. The control unit may be used to carry out control processes to control the medical diagnosis and/or therapy system. A user can control at least one controllable element of the medical diagnosis and/or therapy system using the mobile handheld control unit. The control device is configured such that a set of the control processes can only be carried out by the control unit, when the mobile handheld control unit is located at a predefined location.

Certain control processes are blocked and cannot be executed by the control unit, if the mobile handheld control unit is not located at the predefined location. This enhances the operational safety of the medical diagnosis and/or therapy system compared with a system in which such a control mechanism is not available.

A user, who previously carried out a control operation using the mobile handheld control unit, may position the mobile handheld control unit in an unfavorable position. Subsequent control operations may cause the mobile handheld control unit to be unintentionally damaged or even manipulated in such a manner that it generates control commands in an unintended manner. For example, if the mobile handheld control unit is left on a patient bed and the user leaves the room, so that an imaging examination or radiation session can start, the handheld control unit may be damaged by x-ray beams or by the treatment beam or incorrect functions may be triggered. The damage may have an adverse effect on safety.

In one embodiment, the control device ensures that the mobile handheld control unit is located at a predefined location before certain control processes may be carried out by the control unit. Accordingly, the mobile handheld control unit is not damaged by a control operation of the medical diagnosis and/or therapy system. The operational safety of the medical diagnosis and/or therapy system and patient safety may be increased as a result.

The predefined location within the medical diagnosis and/or therapy system may be located, for example, within a diagnosis and/or therapy room, such as outside the range of moving elements within the diagnosis and/or therapy room and/or outside the active range of diagnosis and/or therapy devices. However, the predefined location may be located outside the diagnosis and/or therapy room. The control unit may be located outside the diagnosis and/or therapy room.

The control device, such as the control unit, does not have to be a single, self-contained unit. The control device may include a number of distributed sub-units, each controlling different elements.

In one embodiment, the control device includes a position monitoring system, which can determine whether or not the mobile handheld control unit is located at the predefined location. Any now known position monitoring system and/or location system may be used as the position monitoring system and/or location system, for example, position monitoring systems operating with electromagnetic waves or acoustic waves.

Position monitoring may be continuous or at certain times, for example, directly during implementation of the control process. The control process may be carried out when the mobile handheld control unit is located at the predefined location.

In one embodiment, the control device may have a holding device for the mobile handheld control unit. The predefined location may correspond to the place in the holding device. For example, the set of control processes may be carried out when the mobile handheld control unit is located in the holding device. The handheld control unit ensures that the mobile handheld control unit is located in its correct place.

The mobile handheld control unit may be a cordless handheld control unit. Control commands from the handheld control unit may be transmitted wirelessly to the control unit.

In one embodiment, the set of control processes, which may be executed by the control unit only when the mobile handheld control unit is located at the predefined location, includes control of the controllable element that can be controlled by a user using the mobile handheld control unit. This allows regulation of a control hierarchy of the controllable element in a simple manner. If the mobile handheld control unit is not located at the predefined location, as a user is operating the mobile handheld control unit, for example, control of the controllable element by the control unit may be blocked. The controllable element may only be operated by the mobile handheld control unit in normal operation. Control of the controllable element may be taken over by the control unit when the mobile handheld control unit is at the predefined location, for example, in a holding device. Interfering or contradictory control instructions may be avoided. The controllable element may be a moving element in a diagnosis and/or therapy room, such as in a patient positioning device and/or an imaging device. In a particle therapy system, the moving element may be a gantry that may be rotated around a radiation room.

If the mobile handheld control unit moves components, such as the imaging device or patient positioning device, for example, a user operating the mobile handheld control unit is protected against unintended control of the components by the control unit. Control of the components by the control unit may endanger a user, if the user was within the radius of movement of the moving components.

In one embodiment, a set of control processes, which may only be executed by the control unit when the mobile handheld control unit is located at the predefined location, includes control of a further controllable element, which cannot be controlled by a user using the mobile handheld control unit. This allows a control hierarchy of different elements, which are controlled by different units, such as the mobile handheld control unit and the control unit, to be regulated in a simple manner, so that safety is enhanced when controlling the medical diagnosis and/or therapy system. Controllable elements, which may not be controlled by a mobile handheld control unit by way of control processes, may be accelerator units to accelerate particles and/or a high-energy beam transportation system in particle therapy.

In one embodiment, a control device is a control device for a particle therapy system. One of the control processes of the control unit is the outputting of a beam release signal. A beam release signal may be present in a particle therapy system, when all the relevant safety checks have been carried out before a planned radiation. Irradiation of an object to be irradiated may only take place when a beam release signal is present. A beam release signal may only be output by the control unit, when the mobile handheld control unit is located at the predefined location. This ensures that the mobile handheld control unit is not erroneously left in the region of the treatment beam, so that it would be damaged during a subsequent irradiation.

In one embodiment, a medical diagnosis and/or therapy system includes a diagnosis and/or therapy device, which is controlled by a control device and a controllable element, which is controlled by the mobile handheld control unit of the control device.

A method for controlling a medical diagnosis and/or therapy system may include one or more control processes to control the medical diagnosis and/or therapy system. The method may include carrying out the one or more control processes. One or more of the control processes may be carried out when a mobile handheld control unit, with which at least one controllable element can be controlled by a user, is located at a predefined location.

BRIEF DESCRIPTION OF THE DRAWINGS

FIG. 3 shows one embodiment of a control process.

DETAILED DESCRIPTION

Figure 1:
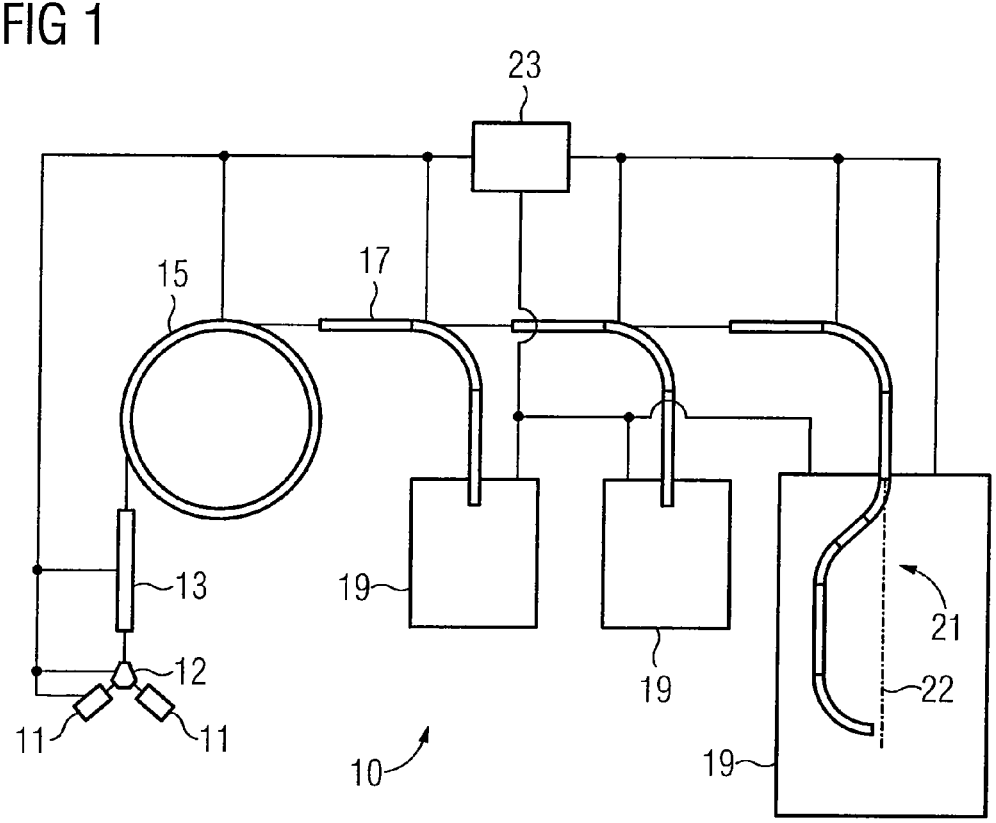
FIG. 1 shows one embodiment of a particle therapy system.

FIG. 1 shows a particle therapy system 10. The particle therapy system 10 may use a particle beam to irradiate a body, such as tumorous tissue.

The particles used may be ions, such as protons, pions, helium ions, carbon ions or other types of ions. Particles are generated in a particle source 11. As shown in FIG. 1, two particle sources 11 may be used to generate two different types of ions. The system 10 may switch between these two different types of ions within a short time interval. A solenoid switch 12, for example, is used for switching. The switch 12 may be arranged between the ion sources 11 and a preaccelerator 13. This allows the particle therapy system 10 to be operated with protons and carbon ions at the same time, for example.

The ions generated by the one or more ion sources 11 and in some instances selected using the solenoid switch 12 are accelerated to a first energy level in the preaccelerator 13. The preaccelerator 13 is, for example, a linear accelerator (LINAC). The particles are fed (transported) into an accelerator 15, for example, a synchrotron or cyclotron. In the accelerator 15 the particles are accelerated to the high energies required for irradiation. When the particles leave the accelerator 15, a high-energy beam transportation system 17 conveys (transports) the particle beam to one or more radiation rooms 19. In a radiation room 19 the accelerated particles are directed onto a body to be irradiated, for example, from a fixed direction (in a fixed beam room) or from different directions using a rotatable gantry 21 that can be moved about an axis 22.

The basic structure of a particle therapy system 10 shown in FIG. 1 is typical of many particle therapy systems but can also differ from this; for example, depending on particle acceleration, a radiation device does not have to be arranged as a particle therapy system.

The particle therapy system 10 may include a number of controllable elements, which are located both outside radiation rooms 19, such as the accelerator and beam guide components, and also inside the radiation rooms 19, such as patient positioning devices and imaging devices. The controllable elements may be controlled by a control unit 23. The control unit 23 does not have to be set up as an individual self-contained unit but may include a plurality of sub-units, each controlling different controllable elements.

Figure 2:
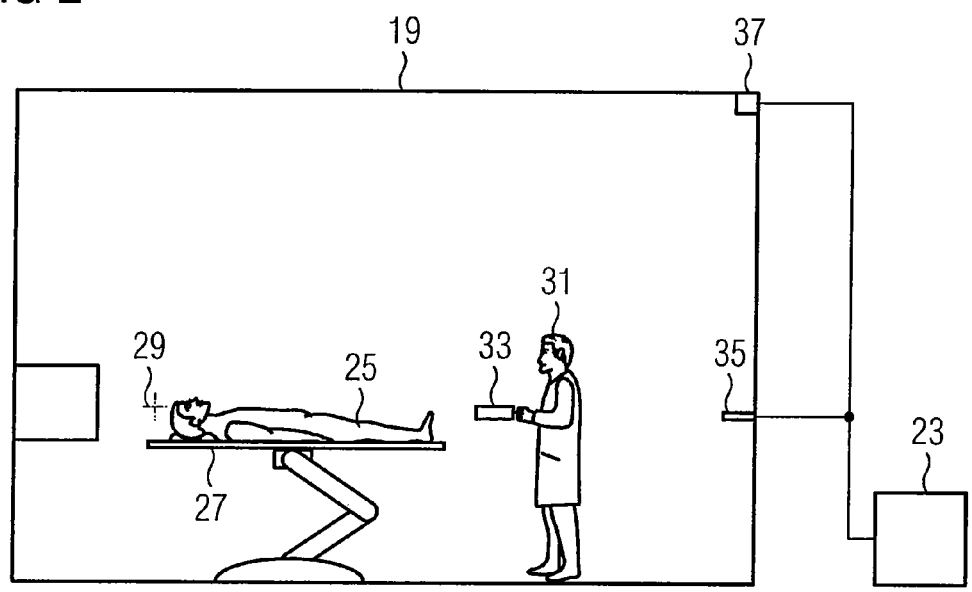
FIG. 2 shows one embodiment of a radiation room, in which a user can execute a control process using a mobile handheld control unit.

FIG. 2 shows a schematic overview of a radiation room 19. In a radiation room 19 an object to be irradiated, such as a patient 25, may be positioned on a positioning device 27. The object to be irradiated may be positioned in relation to an isocenter 29 using the positioning device 27, so that a spatially defined relationship between a particle beam and the object to be irradiated may be maintained.

The controllable elements, for example, the positioning device 27, may be controlled wirelessly by a user 31 using a mobile handheld control unit 33. The mobile handheld control unit 33 may allow a user 31, for example, to remain in proximity to the patient 25, to tend to the patient 25, for example, and at the same time to control the positioning device 27.

A holding device 35 for the mobile handheld control unit 33 may be located in the radiation room 19. The holding device 35 may be a charging cradle for the mobile handheld control unit 33, so that a battery unit of the mobile handheld control units 33 may be charged. The holding device 35 is configured so that holding device 35 identifies whether or not the mobile handheld control unit 33 is located in the holding device 35. This information is supplied to the control unit 23. Certain control processes, which are executed by the control unit 23, may only be executed by the control unit 23, when the mobile handheld control unit 33 is located in the holding device 35.

One of these control processes may, for example, be the outputting of a beam release signal by the control unit 23. A beam release signal is a particle beam that may be directed onto an object to be irradiated. In the absence of a beam release signal, the application of a particle beam is blocked. In one embodiment, the mobile handheld control unit 33 must be located at a predefined location (e.g., the holding device 35) to allow a beam release signal. Further conditions may have to be satisfied, for it to be possible for a beam release signal to be output, for example, correct operation of acceleration and beam guide components. This ensures that the mobile handheld control unit 33 is located at a safe location before irradiation starts and has not accidentally been left in proximity to the patient 25, for example, in proximity to the particle beam.

Another control process may be control of the positioning device 27 by the control unit 23, for example. The positioning device 27 may be controlled by the control unit 23, when the mobile handheld control unit 33 is located at the predefined location. No contradictory control commands may be given when controlling the positioning device 27, as a hierarchy is uniquely defined for control of the positioning device 27.

Alternatively and/or additionally the position of the mobile handheld control unit 33 may be determined, for example, by a position monitoring system 37, which is located in the radiation room.

FIG. 3 shows a control process, which is carried out to control a medical diagnosis and/or therapy system.

As shown in FIG. 3, different control processes 41, 41' may be executed for control purposes. For a set 43 of control processes, the control processes 41' belonging to the set 43 may only be executed, if a certain condition 45 is met. This condition is met when a mobile handheld control unit, which is used to control a controllable element of the medical diagnosis and/or therapy system, is located at a predefined location within the medical diagnosis and/or therapy system. If this condition 45 is not met, the control processes 41' belonging to the set 43 cannot be activated. The control processes 41' belonging to the set 43 can be control processes, which control the controllable element, which may be controlled by the mobile handheld control unit. The control process belonging to the set may be a control process, which is used to control further controllable elements, which cannot be controlled by the mobile handheld control unit.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A control device for a medical system, the control device comprising:
   a control unit configured to carry out control processes that control the medical system, and
   a mobile handheld control unit in communication with the control unit and configured to control a first controllable element of the medical system by a user,
   wherein the control device is configured so that one or more of the control processes are only carried out by the control unit when the mobile handheld control unit is located at a predefined location,
   wherein the control device is configured to control a second controllable element of the medical system, the second controllable element not controllable by the mobile handheld control unit regardless of location of the mobile handheld control unit,
   wherein the medical system is a particle therapy system, and the control unit is configured to output a beam release signal, and
   wherein the control device is configured to output, as a first control process of the one or more control processes, the beam release signal only when the mobile handheld control unit is located at the predefined location.

2. The control device as claimed in claim 1, further comprising a position monitoring system that is configured to determine whether the mobile handheld control unit is located at the predefined location.

3. The control device as claimed in claim 1, wherein the predefined location is a location in a holding device for the mobile handheld control unit.

4. The control device as claimed in claim 1, wherein the mobile handheld control unit is a cordless handheld control unit.

5. The control device as claimed in claim 1, wherein the control device is configured to control, as a second control process of the one or more control processes, the first controllable element of the medical system by the user using the mobile handheld control unit only when the mobile handheld control unit is located at the predefined location.

6. The control device as claimed in claim 1, wherein the control device is configured to control, as a second control process of the one or more control processes, the second controllable element only when the mobile handheld control unit is located at the predefined location.

7. The control device as claimed in claim 1, wherein the medical system is a medical diagnosis system, a medical treatment system, or a medical diagnosis and treatment system.

8. A medical system comprising:
   a diagnosis device, a therapy device, or a diagnosis and therapy device including a first controllable element, and
   a control device including a control unit and a mobile handheld control unit, the control unit being configured to carry out a control process that controls the first controllable element of the diagnosis device, the therapy device, or the diagnosis and therapy device, only carried out by the control unit when the mobile handheld control unit is located at a predefined location,
   wherein the control device is configured to control, as a first control process of the one or more control processes, a second controllable element of the diagnosis device, the therapy device, or the diagnosis and therapy device only when the mobile handheld control unit is located at the predefined location, the second controllable element not controllable by the mobile handheld control unit,
   wherein the medical system is a particle therapy system, and the control unit is configured to output a beam release signal, and
   wherein the control unit is configured to output, as a second control process of the one or more control processes, the beam release signal only when the mobile handheld control unit is located at the predefined location.

9. A method for controlling a medical diagnosis system, a medical therapy system, or a medical diagnosis and therapy system, the method comprising:
   carrying out one or more control processes to control the medical diagnosis system, the medical therapy system, or the medical diagnosis and therapy system when a mobile handheld control unit is located at a predefined location, and
   controlling, with the mobile handheld control unit, a first controllable element of the medical diagnosis system, the medical therapy system, or the medical diagnosis and therapy system,
   wherein the one or more control processes includes controlling a second controllable element that cannot be controlled by the mobile handheld control unit,
   wherein carrying out the one or more control processes includes carrying out a beam release only when the mobile handheld control unit is located at the predefined location, and
   wherein carrying out the beam release includes releasing a particle beam for irradiation.

10. The method as claimed in claim 9, further comprising monitoring a position of the mobile handheld control unit and determining whether the mobile handheld control unit is located at the predefined location.

11. The method as claimed in claim 9, wherein carrying out the one or more control processes when the mobile handheld control unit is located at the predefined location comprises carrying out the one or more control processes when the mobile handheld control unit is located in a holding device for the mobile handheld control unit.

12. The method as claimed in claim 9, wherein carrying out the one or more control processes when the mobile handheld control unit is located at the predefined location comprises carrying out the one or more control processes when a cordless handheld control unit is located at the predefined location.

13. The method as claimed in claim 9, wherein the one or more control processes includes controlling the first controllable element, which is controllable by the user using the mobile handheld control unit.

14. The method of claim 9, wherein controlling the second controllable element comprises controlling an accelerator of the medical diagnosis system, the medical therapy system, or the medical diagnosis and therapy system to form a beam, the mobile handheld control unit not being operable to control the accelerator to form the beam, and
   wherein carrying out the one or more control processes comprises controlling the accelerator only when the mobile handheld control unit is located at the predefined location.

* * * * *